US006406852B1

(12) United States Patent
Tuli et al.

(10) Patent No.: US 6,406,852 B1
(45) Date of Patent: Jun. 18, 2002

(54) METHOD FOR PREPARATION OF MICROPROJECTILES FOR EFFICIENT DELIVERY OF BIOLOGICALS USING A PARTICLE GUN

(75) Inventors: Rakesh Tuli; Samir V. Sawant, both of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/599,802

(22) Filed: Jun. 22, 2000

(51) Int. Cl.$^7$ .......................... C12Q 1/68; C12N 15/64
(52) U.S. Cl. ........................ 435/6; 435/459; 435/470
(58) Field of Search ................. 435/459, 470, 435/6

(56) References Cited

U.S. PATENT DOCUMENTS 5,756,322 A * 5/1998 Tumer ..................... 435/172.1

OTHER PUBLICATIONS

Sawant, S. V., et al., "Pretreatment of Microprojectiles to Improve the Delivery of DNA in . . . ", Biotechniques, vol. 29, No. 2, (2000), pp. 246–248.
Sawant, S., et al., "Designing of an artificial expression cassette for the . . . ", Theor Appl Genet, vol. 102, (2001), pp. 635–644.
Sawant, S., et al., "Sequence Architecture Downstream of the Initiator Codon . . . ", Plant Physiology, vol. 126, (2001), pp. 1630–1636.
Gordon–Kamm, W. J., et al., "Transformation of Maize Cells and Regeneration of Fertile . . . ", The Plant Cell, vol. 2, 1990, pp. 603–618.
Finer, J. J., et al., "Transformation of cotton (Gossyplum hirsutum L.) via particle . . . ", Plant Cell Reports, vol. 8, 1990, pp. 586–589.
Ellis, D. D., et al., "Stable Transformation of Picea glauca by Particle Acceleration", Bio/Technology, vol. 11, 1993, pp. 84–89.
Jain, R. K., et al., "Optimization of biolistic method for transient gene expression . . . ", Plant Cell Reports, 1996, pp. 963–968.

* cited by examiner

*Primary Examiner*—James Ketter
(74) *Attorney, Agent, or Firm*—Ladas & Parry

(57) ABSTRACT

The present invention relates to a process for uniform and efficient delivery of metal projectiles into living cells and tissue of plants and animals, by bombarding the cells with biological coated on metal bead particles. The metal bead particles are heated in dry oven to high temperature, prior to coating with DNA and by substituting ethanol with isopropanol while coating the particles with DNA, to give several fold higher expression of the nucleic acid delivered into cells.

10 Claims, No Drawings

US 6,406,852 B1

METHOD FOR PREPARATION OF MICROPROJECTILES FOR EFFICIENT DELIVERY OF BIOLOGICALS USING A PARTICLE GUN

FIELD OF INVENTION

The present invention relates to a process for delivery of biological materials into living cells and tissues of plants and animals. More particularly, this invention relates to a process wherein, the biomolecules to be delivered into cells are coated on tiny inert particles, called microprojectiles, which are then bombarded on the target cells or tissues. The microprojectiles are coated with biological materials, like nucleic acids and delivered into cells, using a microprojectile gun, also called as 'gene gun' or 'biolistic gun'. Commonly used microprojectiles are gold and tungsten particles. The improved process claimed here gives highly efficient, more uniform and reproducible delivery of microprojectiles. As a result, it gives several fold higher expression of the nucleic acid delivered into cells.

BACKGROUND OF INVENTION

Accelerated metal particles coated with nucleic acids are extensively used for introducing genes into intact plants and animals, tissues, cells and organelles (Sanford et al., 1993 Sanford J. C., Smith F. C. and Russell, J. A. 1993 Optimising the biolistic process for different biological applications. Methods in Enzymology, 217, 485–510). A variety of particle guns that deliver microprojectiles into living cells have been described in earlier inventions (U.S. Pat. Nos. 5,100,792, 5,179,022, 5,204,253 and 5,865,796). Though several different types of particles have been discussed, including high density metals like gold, tungsten, platinum, ferrite etc., and low density synthetic polymeric particles (U.S. Pat. No. 5,783,567), the former group has been more successful apparently because these can be delivered with higher kinetic energy and can therefore, go deeper into the target tissue. Gold particles have been more commonly used because gold is more inert than others, i.e., it does not interfere with biological processes and the gold particles have more uniform surface, desirable for minimum cell damage.

The particles are coated with the biological material to be delivered into living cells. The microprojecticles, coated with the biological material are then propelled at high speed, using one of a variety of particle guns made by certain research groups or available commercially.

Accelerated metal particles penetrate several layers deep into tissue, depending upon the velocity and momentum at which these strike the target tissue. The acceleration to particles can be provided by mechanical impulse, centripetal force, electric discharge (U.S. Pat. No. 5,100,792), firing explosives (U.S. Pat. No. 5,179,022) or compressed gas (U.S. Pat. No. 5,865,796) or any other process. The most commonly used and commercially available apparatus for acceleration of microprojectiles involves acceleration using gas shock (U.S. Pat. Nos. 5,204,253 and 5,865,796) and is available commercially from M/S Bio-Rad Laboratories, Hercules, Calif. 94547, USA.

Examples of biological substances that can be coated onto or impregnated into inert particles include biological stain such as fluorescent or radioactive probes, viruses, organelles, proteins, hormones and nucleic, acids. In certain cases delivery of molecules into cells and tissues under liquid pressure has also been claimed (U.S. Pat. No. 5,766,901).

The effectiveness of the delivery of particles is most conveniently measured by examining the expression of a reporter gene delivered in form of DNA coated on such particles. One of the very commonly used reporter genes is uidA (Jefferson, R. A. and Wilson, K. J. 1991. The GUS gene fusion system In: S. Gelvin and R. Schilperoort Ed. Plant Molecular Biology, Kluwer Academic Publishers, Dordrecht, B 14, pp. 1–33) which codes for an enzyme called glucuronidase. Once the gene is inside a cell and if the cell is viable, the gene makes the enzyme glucuronidase. Following bombardment of uidA gene containing particles, if a plant leaf is treated with a chromogenic substrate 5-bromo-4-chloro-3 indoyl-$\beta$-D-glucuronic acid, also called X-gluc, it is converted into a blue product due to activity of glucuronidase. The blue spots appear on the bombarded leaf and can be counted by treating the leaf with X-gluc, one to several days after bombardment. Therefore, the number of spots indicate the number of foci within target tissue where particles get delivered without causing significant damage to biological function of cells. Hence, expression of glucuronidase is indicative of delivery of the microprojectile particles in a manner that did not cause damage to biological function of the cell. Therefore, efficiency of biologically effective delivery of microprojectile particles can be measured by counting under microscope, blue spots on the leaf surface for example, in case of plants (or any other tissue) that are formed due to expression of glucuronidase. This method is called as 'histochemical method' since it allows seeing the activity by color. It is not quantitative but qualitative since it tells the presence of activity but does not quantitatively measure the level of glucuronidase activity. Details of this method, as applied to gold and tungsten coated particles are also given in Ratnayaka and Oard (1995, I. J. S. Ratnayaka and J. H. Oard 1995 A rapid method to monitor DNA precipitation onto microcarriers before particle bombardment, Plant Cell Reports, 14, 794–798).

A second more sensitive method to measure the activity of $\beta$-glucuronidase after microprojectile bombardment is by quantitatively measuring the formation of a fluorescent product. In this method, a non fluorescent substrate called 4-methlyumbelliferyl-$\beta$-D-glucuronide, also called MUG, is converted by glucuronidase into a fluorescent product called MU. Hence, the increase in fluorescence per mg protein in leaf gives quantitative expression of gene delivery in a manner that did not damage biological function of the target, cells. The less the expression, the less successful the delivery of DNA coated on microprojectiles. The fluorometeric as well as histochemical GUS assays are also described in Kloti et al (1999, A. Kloti, C. Henrich and others in Plant Molecular Biology, 40, 249–266). Both of these standard methods were employed in this invention to illustrate an amazingly high improvement of results obtained by the bombardment protocol claimed by us.

While coating microprojectiles with DNA the procedure recommended by Bio-Rad Laboratories in their catalogue or its minor variations are commonly used. This method is based on the original method developed by Sanford et al. (1993, J. C. Sanford, F. D. Smith and J. A. Russell, 1993 optimising the biolistic process for different biological applications, Meth. Enzymol. 217, 483–509). In this method, 3 mg gold particles (1 $\mu$m diameter particles for example, supplied by, Bio-Rad Laboratories, USA) are placed in a microcentrifuge tube and vortexed for 3 min in 0.5 ml 70% ethanol (v/v). The suspension is held at room temperature for 10 min, centrifuged (15000 rpm) for 5 sec and decanted. The pellet of particles is washed three times with 500 $\mu$l sterile distilled water. Between two washings, the suspension is mixed thoroughly by vortexing for 1 min, the particles are allowed to settle on bench for 1 min and then centrifuged for 5 sec. Finally, the washed particles are suspended in 50 µl of 50% glycerol. The suspended particles are then coated with DNA by adding 5 µl DNA (1 µg/µl in water), 50 µl $CaCl_2$ (2.5 M) and 20 µl spermidine (0.1 M stock) in that order, vortexed for 3 min, held at room temperature for 5 min, and finally the coated particles are pelleted by pulse centrifugation. The preparation is then washed with 150 µl of 70% ethanol, followed by absolute ethanol before they are suspended in 48 µl ethanol. The coated particles are then vortexed for 1 to 2 seconds before placing 8 µl aliquots on macrocarrier for bombardment on a target tissue, like tobacco leaf. The above commercially recommended procedure given by Bio-Rad Laboratories Ltd. Along with the Helium Drive PDS-1000/He system Biolistic Gun is stated in US/EG Bulletin 1688 by BioRad Life Science Group, California. Hunold et al. (1994, R. Hunold, R. Bronner and G. Hahne, 1994 Early events in microprojectile bombardment: Cell Viability and Particle location. Plant J. 5, 593–604) suggested minor variation in the above described method developed by Sanford. The method of Hunold et al. (1994) is also used commonly. The method of Hunold et al. (1994) was used in this study and is referred to as "Standard Method". In the standard method, 3 mg gold particles (1 µm diameter particles for example, supplied by, the Bio-Rad Laboratories, USA) are placed in a microcentrifuge tube and vortexed for 3 min in 0.5 ml 70% ethanol (v/v). The suspension is sonicated for 2 sec in water bath sonicator (Branson, USA), held at room temperature for 15 min, centrifuged (15000 rpm) for 5 sec and decanted. The pellet of particles is washed three times with 500 µl sterile distilled water. Between two washings, the suspension is mixed thoroughly by vortexing for 1 min, the particles are allowed to settle on bench for 1 min and then centrifuged for 5 sec. Finally, the washed particles are suspended in 50 µl of 50% glycerol and sonicated for 2 sec in water bath sonicator (Branson, USA). The suspended particles are then coated with DNA by adding 5 µl DNA (1 µg/µl in water), 50 µl $CaCl_2$ (2.5 M) and 20 µl spermidine (0.1 M stock) in that order, vortexed for 3 min, held at room temperature for 5 min, and finally the coated particles are pelleted by pulse centrifugation. The preparation is then washed with 150 µl of 70% ethanol, followed by absolute ethanol before they are suspended in 48 µl ethanol. The coated particles are then vortexed for 1 to 2 seconds before placing 8 µl aliquots on macrocarrier for bombardment, for example, at 1100 psi on tobacco leaf placed at 12.3 cm target distance. A helium driven particle gun PDS-1000He (Bio-Rad, U.S.A.) is commonly used. In this study, the bombarded leaves were incubated on MS agar medium. The glucuronidase activity was examined histochemically by counting the total number of blue spots as well as measured quantitatively fluorimetrically, as in published procedures cited above. A few other minor variations of the above procedure for coating microprojectiles with DNA are given in several references including their applications to maize cells (Klein et al 1988, BioTechnology, 6, 559–563), tobacco plastids (Svab et al, 1990, Proc. Natl. Acad. Sci USA, 87, 8526–8530), tobacco cells (Russell et al, 1992 In vitro Cell Dev. Biol. 28 P, 97–105), micro-organisms and animals (Klein et al, BioTechnology, 10, 286–291), mammalian cells (Heiser, 1994, Analytical Biochemistry, 217, 185–196), plant pollens (Stoger et al, 1995, Plant Cell Reports, 14, 273–278) and several others. Standardization is required to optimize the pressure at which the particles are bombarded on target tissue, At a given particle acceleration (determined by gas pressure and the distance between the point of discharge of particles and the target tissue), the conditions discussed in the above modified procedures make minor differences in efficiency of biologically active DNA delivery into target tissue.

A major difficulty encountered in the bombardment of microprojectiles in the above studies including the above described methods by Sanford et al. (1993) and Hunold et al. (1994), is that the particles of heavy metals like gold and tungsten agglomerate, leading to their non uniform spread following bombardment on the target tissue. The tendency of particles to stick to one another results in the formation of clumps. The particles also stick to the walls of container, like polypropylene tubes in which these are prepared. Sticking to the container and to one another results in loss of substantial amount of particles and DNA and variability in the precipitation of DNA and non reproducible shot-to-shot results (Vain et al., 1993 Plant Cell, Tissue and Organ Culture, 33, 237–246). Delivery of clumps on tissues also results in irreparable damage to target tissue (Ratnayaka & Oard, 1995 Plant Cell Reports 14, 794–798). Use of certain expensive brands of microcentrifuge tubes has been suggested (Sanford et al., 1993 Methods in Enzymology, 217, 483–510) to reduce sticking of the particles to surface of the tube. Although vigorous vortexing, ultrasonication, use of glycerol or polyethylene glycoll are claimed to reduce aggregation, uniform and efficient delivery of the microprojectiles for reproducible results continues to be a major problem (Sanford et al., 1993 Methods in Enzymology, 217, 483–510). Variability in the results from individual bombardment events is so high that an internal control is used in all experiments to allow normalization of such variations between independent experiments, treatments and replicates (see for example, Bruce et al, 1989, Proc. Natl. Acad. Sci USA, 86: 9692–9696; Schledzewski and Mendel, 1994, Transgenic Research 3, 249–255; Schenk et al, 1998, Plant Mol. Biol. Reporter, 16, 313–322).

In a recent patent (U.S. Pat. No. 5,879,918 dated Mar. 9, 1999) Tomes and coworkers claimed an improvement wherein they 'cleaned' the tungsten beads with strong nitric acid while agitating those continuously by sonication during the pretreatment. The pretreatment claimed by them gave an average of about two to thee fold improvement in the expression of β-glucuronidase, following the delivery of reporter gene DNA using tungsten or gold particles on cells of maize plant. The gain was rather small and the shot to shot variation was not controlled by the method claimed by them. Our invention relates to a new method for pretreatment of the metal particles and coating of DNA. The method described here gives 43 to 63 fold enhancement in delivery of the particles, depending upon the method of measurement and the batch of particles used to deliver DNA molecules onto plant leaf tissue. Our improved method does not involve use of strong acids like nitric acid as a step of pretreatment. It reduces shot-to-shot variation to the statistically acceptance level of average 6.7% as compared with the unacceptable variation of 43% obtained by the standard process.

OBJECT OF THE INVENTION

The main object of the invention is to develop a method for uniform and efficient delivery of metal microprojectiles into living cells by bombarding the cells with such particles. The preferred particles are gold particles.

Another object of the present invention allows coating of the gold particles with biological material, preferred biological material being DNA, in such a manner that the particles do not stick to one another or to the walls of container, being polypropylene tube as the preferred container.

SUMMARY OF THE INVENTION

The present invention achieves the above objectives by heating the gold particles in dry oven to high temperature, prior to coating with DNA and by substituting ethanol with isopropanol while coating the particles with DNA. Using Helium driven PDS 1000/He (BioRad Laboratories) as the preferred biolistic gun, the resultant particles are delivered extremely efficiently, uniformly and reproducibly in the cells of leaf tissue, used as the preferred biological tissue. Dry heat at high temperature apparently removes the water molecules and possibly other volatile substances that are tightly adsorbed on gold particles. Removal of such molecules prevents agglomeration of gold particles, thus giving highly uniform spread of the particles in target tissues. The uniform spread also prevents the damage caused to tissue if the particles are bombarded as bigger clumps. The DNA delivered by the new method expresses in the target tissue at levels 20 to 70 fold higher than that by the commonly used and recommended methods and publicly published by Bio-Rad Life Science Group and several others. The improved method works highly efficiently irrespective of the conditions under which the particles were stored prior to the usage.

DETAILED DESCRIPTION OF THE INVENTION

In the process claimed here, the preferred gold particles were first pretreated by heating those at high temperature in a dry oven for several hours before preparing those for coating with DNA. The temperature of heating and the duration of heating are not critical. High temperature and sufficient time are required that would permit the removal (including the removal of water molecules) of unknown interfering residues that adhere to the gold (or tungsten) particles. It is also possible that the heating makes certain chemical or physico chemical changes on the surface of particles. Such undesired molecules may get adsorbed from the surroundings or may get formed on metal particles during their manufacture, transportation or storage. At the lower end, heating for 1 hour at 150° C. was helpful. Routinely, the particles were pretreated by heating at 150° C. for over-night. The temperature of heating was not critical but generally can range from 80° C. to 200° C. or higher.

The preheated particles were then used to coat with DNA by a standard procedure except that ethanol was substituted at all steps with isopropanol. A standard procedure (Sanford et al., 1993, Methods in Enzymology, 217, 483–510) is as follows:

In a "Standard Method", as described earlier 3 mg gold particles (1 $\mu$m diameter particles for example, supplied by, Bio-Rad Laboratories, USA) are placed in a microcentrifuge tube and vortexed for 3 min in 0.5 ml 70% ethanol (v/v). The suspension is sonicated for 2 sec in water bath sonicator (Branson, USA), held at room temperature for 15 min, centrifuged (15000 rpm) for 5 sec and decanted. The pellet of particles is washed three times with 500 $\mu$l sterile distilled, water. Between two washings, the suspension is mixed thoroughly by vortexing for 1 min, the particles are allowed to settle on bench for 1 min and then centrifuged for 5 sec. Finally, the washed particles are suspended in 50 $\mu$l of 50% glycerol and sonicated for 2 sec in water bath sonicator (Branson, USA). The suspended particles are then coated with DNA by adding 5 $\mu$l DNA (1 $\mu$g/$\mu$l in water), 50 $\mu$l $CaCl_2$ (2.5 M) and 20 $\mu$l spermidine (0.1 M stock) in that order, vortexed for 3 min, held at room temperature for 5 min, and finally the coated particles are pelleted by pulse centrifugation. The preparation is then washed with 150 $\mu$l of 70% ethanol, followed by absolute ethanol before they are suspended in 48 $\mu$l ethanol. The coated particles are then vortexed for 1 to 2 seconds before placing 8 $\mu$l aliquots on macrocarrier for bombardment, for example, at 1100 psi on tobacco leaf placed at 12.3 cm target distance. A helium driven particle gun PDS-1000He (Bio-Rad, U.S.A.) is commonly used. In this example, the bombarded leaves are incubated on MS agar medium. The glucuronidase activity is examined histochemically by counting the total number of blue spots as well as is measured quantitatively fluorimetrically, as in published procedures (Jafferson and Wilson, 1991 In Plant Molecular Biology Manual, Kluwer pp. 1–33). In the improved procedure claimed by us, all other steps were executed as described above, except that the gold particles were heated at 90 to 200° C. over-night in a glass tube before use in the above procedure and that ethanol was substituted with isopropanol, HPLC (Spectrochem, India) grade in the steps described above. Other alcohols like isopropanol (primary alcohol) and isoforms of butanol, specially volatile alcohols with low solubility in water and acetone were tried and are obvious alternatives that may work at varying efficiencies.

Accordingly the invention provides, an improved process for transporting a biological material into living cells which comprises bombarding the said cells with a biological material coated on metal bead particles, wherein the improvement comprises in pretreating the metal bead particles by heating the said particles at a temperature ranging between 90–300° C. for a period ranging between 1 to 18 hours and thereafter coating the said pretreated bead particles with a biological material using an organic solvent.

In an embodiment of the present invention, the heating of the particles is carried out in a dry oven to allow removal of volatile materials.

In an embodiment of the present invention, the particles used are beads selected from any biologically non reactive materials from the group consisting of gold, palladium, platinum or any alloy thereof.

In an embodiment of the present invention, the particles used are beads selected from any biologically non reactive materials from the group consisting of gold, palladium, platinum or any alloy thereof which may be either new or old.

In another embodiment of the present invention, the old particles used are beads selected from any biologically non reactive materials from the group consisting of gold, palladium, platinum or any alloy thereof stored for a period of more than six months.

In another embodiment of the present invention, the beads used have a diameter of from about 0.1 microns to about 3.0 microns.

In yet another embodiment of the present invention, the heat pretreated particles are used for coating of biological material using standard protocols for coating DNA or RNA or other biologically active molecules on metal particles to be used for delivery into cells.

In yet another embodiment of the present invention, the heat treated particles are used for coating of biological materials using isopropanol to prevent clumping of particles or their sticking to walls of the container.

In still another embodiment of the present invention, the particles with or without heat pretreatment are coated with a biologically material by known methods.

In an advantageous embodiment of the present invention, the biological material used is DNA or RNA or another biologically active molecule to be delivered in cells or tissue using microprojectiles as carriers.

In another advantageous embodiment of the present invention, the biological molecules are delivered in the cell to study transient or long term effects of the delivery of the molecules on the living systems including vaccination and drug delivery and their effect within that or in subsequent generations.

The following examples are given to illustrate but not necessarily limit the parameters of the present invention. The examples illustrate that the process of preparing particles for biolistic delivery of DNA, as described in the present invention is several fold more effective and reproducible than the conventional methods.

EXAMPLE 1

In this example, the benefit of pretreatment i.e., heating the gold particles before coating with DNA is illustrated to get improved gene expression following delivery of the particles. Two batches of gold microprojectiles (1 $\mu$m particles) obtained from M/S Bio-Rad Laboratories, USA were used to illustrate utility of the protocol developed by us. The 'old batch' of gold particles was received from Bio-Rad, USA in July 1996 i.e. about 3 years back while the 'new batch' was received recently in August 1999. Both the batches were stored at room temperature in the vials, as supplied and without any special arrangements, as recommended by the manufacturer. The helium driven particle gun PDS-1000 He which is a proprietary equipment used world wide and supplied under a lease-license agreement by Bio-Rad Laboratories, USA was used.

The standard procedure recommended by Hunold et al. (1994, R. Hunold, R. Bronner and G. Hahne, 1994 Early events in microprojectile bombardment: Cell Viability and Particle location. Plant J. 5, 593–604) was used for coating the particles with DNA. The standard method was as follows:

In a "Standard Method", 3 mg gold particles (1 $\mu$m diameter particles for example, supplied by, Bio-Rad Laboratories, USA) are placed in a microcentrifuge tube and vortexed for 3 min in 0.5 ml 70% ethanol (v/v). The suspension is sonicated for 2 sec in water bath sonicator (Branson, USA), held at room temperature for 15 min, centrifuged (15000 rpm) for 5 sec and decanted. The pellet of particles is washed three times with 500 $\mu$l sterile distilled water. Between two washings, the suspension is mixed thoroughly by vortexing for 1 min, the particles are allowed to settle on bench for 1 min and then centrifuged for 5 sec. Finally, the washed particles are suspended in 50 $\mu$l of 50% glycerol and sonicated for 2 sec in water bath sonicator (Branson, USA). The suspended particles are then coated with DNA by adding 5 $\mu$l DNA (1 $\mu$g/$\mu$l in water), 50 $\mu$l CaCl$_2$ (2.5 M) and 20 $\mu$l spermidine (0.1 M stock) in that order, vortexed for 3 min, held at room temperature for 5 min, and finally the coated particles are pelleted by pulse centrifugation. The preparation is then washed with 150 $\mu$l of 70% ethanol, followed by absolute ethanol before they are suspended in 48 $\mu$l ethanol. The coated particles are then vortexed for 1 to 2 seconds before placing 8 $\mu$l aliquots on macrocarrier for bombardment, for example, at 1100 psi on tobacco leaf placed at 12.3 cm target distance. A helium driven particle gun PDS-1000He (Bio-Rad, U.S.A.) is commonly used. In this example, the bombarded leaves are incubated on MS agar medium. The glucuronidase activity is examined histochemically by counting the total number of blue spots as well as is measured quantitatively fluorimetrically, as in published procedures (Jafferson and Wilson, 1991 In Plant Molecular Biology Manual, Kluwer pp. 1–33).

As claimed in this invention, the above standard method was conducted exactly as outlined above except that 3 mg gold particles were heated at 150° C. over-night in a glass tube before use in the above procedure. These were cooled to room temperature by keeping the glass tube on shelf for 5 minutes or so before use.

An average of six bombardments were done for each of the two treatments. Table 1 gives statistically analysed results, clearly demonstrating the superiority of this invention over the "Standard Method". Expression of glucuronidase was 36 and 23 fold higher respectively when the invention of heat pretreatment was applied to the old and the new batch of gold particles.

TABLE 1

Quantitative estimation of glucuronidase expression by fluorimetric method following delivery of DNA using gold microprojectiles delivered without and with preheating.

| | GUS activity (pmol MU/h/mg protein) | |
|---|---|---|
| Treatment | Old particles | New particles |
| Standard Method | 17.5 ± 11 | 30 ± 13 |
| Heat Pretretment invention | 633 ± 107 | 689 ± 97 |

EXAMPLE 2

In this example of the invention of heat pretreatment step is illustrated to reduce clumping of the particles as seen by uniform spread of biologically active delivery events on the leaf tissue.

The gold particles of the 'old' and the 'new' batch were prepared 'with' and 'without' preheating step, exactly as described in Example 1. The particles were coated with DNA by standard protocol as described except that the preheated particles were in one set of 'old' and the 'new' batch each.

All the four treatments had six replicates each. Unlike Example 1, the bombarded leaves were treated with histochemical substrate X-gluc rather than the fluorescent substrate. Expression of DNA delivery was therefore scored in terms of blue spots per shot that appeared on the leaf, three days after delivery.

The results given in Table 2 clearly show 47 fold and 34 fold more number of spots (suggesting better spread of particles on leaf tissue) following the application of the invention i.e., pretreatment by heating to the old and the new batch of gold particles.

TABLE 2

Estimation of improved spread of particles by histochemical method following delivery of DNA using gold microprojectiles delivered without and with preheating.

| | GUS activity scored as number of blue spots per shot | |
|---|---|---|
| Treatment | Old particles | New particles |
| Standard Method | 112 ± 59 | 178 ± 102 |
| Heat pretreatment invention | 5312 ± 764 | 5986 ± 786 |

EXAMPLE 3

In this example, the benefit of improved DNA coating method wherein ethanol was substituted with propan-2-ol or isopropanol is illustrated in terms of quantitative enhancement of functional reporter gene delivery on leaf tissue.

Exactly as given in example 1, the old and the new batches of gold particles were coated with DNA as per the standard protocol described in example 1. No heat pretreatment of particles was given in any case. Instead, the particles were used directly for coating with DNA. However, in one of the treatments, ethanol in all the steps of standard protocol was substituted with propan-2-ol HPLC grade (from Spectrochem, India). The particles were delivered on tobacco leaf as described. Effectiveness of delivery of DNA was assessed by estimating glucuronidase expression quantitatively by the fluroescent method, as in Example 1 and described in literature.

As seen in results in Table 3, the invention of use of isopropanol instead of ethanol increases gene delivery by about 10 fold for both old and new particles.

TABLE 3

Quantitative expression of glucuronidase expression by fluorescent method using gold particles coated with DNA in ethanol vs isopropanol.

| Treatment | GUS activity (pmol MU/h/mg protein) | |
| --- | --- | --- |
| | Old particles | New particles |
| Standard Method | 17.5 ± 11 | 30 ± 13 |
| Invention - isopropanol | 166 ± 67 | 326 ± 28 |

EXAMPLE 4

This example illustrates the beneficial effect of using isopropanol (instead of ethanol) in the process of coating DNA, on the uniformity of spread of microprojectiles as measured by the number of spots that represent the foci of biologically good delivery of DNA in leaf tissue.

Both the old and the new batches of gold particles were taken to illustrate the beneficial effect. The gold particles were prepared without preheating. These were coated with DNA by the standard protocol as described in Example 1 except that in one treatment ethanol was used while in the improved treatment isopropanol was substituted for ethanol in all the steps. Quality of spread of particles was assessed by histochemical method by scoring blue spots, as described in Example 2.

As shown in Table 4, the isopropanol treatment also improves spread of particles 12 to 15 fold suggesting a significantly improved delivery of particles onto a large number of site in a biologically active manner, in the leaf tissue.

TABLE 4

Estimation of improved spread of particles following ethanol vs isopropanol treatment for coating DNA, following biolistic delivery and measurement by histochemical method.

| Treatment | GUS activity scored as number of blue spots per shot | |
| --- | --- | --- |
| | Old particles | New particles |
| Standard Method | 112 ± 59 | 178 ± 102 |
| Invention - isopropanol | 1365 ± 38 | 2618 ± 262 |

EXAMPLE 5

This example illustrates the combined effect of both heat pretreatment of particles followed by use of isopropanol during coating of DNA as superior to any one of these inventions taken separately. The results show that while each of the two inventions gives substantial advantage over the standard protocol, both the inventions employed together are synergistic and give much better results in terms of both expression of the delivered gene and uniformity of spread of the delivered particles.

In this example, the following four combinations were compared for each of the old and the new particles.

i) Particles without heat pretreatment and coated with DNA in ethanol i.e. standard protocol.

ii) Particles with heat treatment (invention 1) and use of ethanol during DNA coating as per standard protocol.

iii) Particles without heat pretreatment and coated with DNA in isopropanol (invention 2) substituted at all the steps instead of ethanol.

iv) Particles with heat treatment (invention 1) as well as use of isopropanol instead of ethanol (invention 2) during DNA coating.

The above four treatments were applied to both old batch of gold particles as well as the new batch. As seen in Table 5, the heating pretreatment gave a dramatic improvement in biologically useful delivery of particles (36 and 23 fold higher for old and new particles respectively). Without the step of heat pretreatment, isopropanol improved the results by about 10 fold. However, once particles were pretreated by heating, use of propanol improved results further by 1.2 fold and 2.1 fold in case of old and new particles respectively. Together, both preheating and isopropanol improved gene delivery by 43 and 46 fold respectively in case of the old and the new particles.

TABLE 5

Quantitative estimation of reporter gene (glucuronidase) expression by fluorimetric method following delivery of DNA using gold microprojectiles treated with both heat and isopropanol.

| | GUS activity (pmol/MU/h/mg protein) | | | |
| --- | --- | --- | --- | --- |
| | Old particles | | New particles | |
| | Ethanol | Isopropanol | Ethanol | Isopropanol |
| Non heated | 17.5 ± 11 | 167 ± 67 (9.5x)* | 30 ± 13 | 326 ± 28 (10.7x) |
| Heated | 633 ± 106 | 758 ± 33 (1.2x)* | 689 ± 97 | 1394 ± 93 (2.1x) |

*Figures in bracket give fold improvement over and above the treatment in the column on immediate left.

As seen in Table 6 also, the beneficial effect of heat pretreatment of particles was much more (47 and 34 fold for old and new particles respectively) than that of isopropanol treatment (12 and 15 fold for old and new particles respectively) during the steps of coating with DNA when spread of biologically functional DNA delivery was measured by the histochemicaly method. Once particles had been subjected to heat pretreatment, the use of isopropanol gave 1.3 and 1.5 fold advantage over and above the benefit already endowed by heat pretreatment. Thus the results, as seen by the histochemical method, are in complete agreement with the results seen by the fluorescence method. It suggests that both the new steps in the invention give improvement by achieving better dispersal of the particles delivered on the target tissue.

TABLE 6

Estimation of spread of particles by histochemical method following delivery of DNA using gold microprojectiles treated with both heat and isopropanol.

GUS activity scored as number of blue spots per shot

|  | Old particles | | New particles | |
| --- | --- | --- | --- | --- |
|  | Ethanol | Isopropanol | Ethanol | Isopropanol |
| Non heated | 112 ± 59 | 1365 ± 238 (12.2x)* | 178 ± 102 | 2618 + 262 (14.7x) |
| Heated | 5312 ± 764 | 7117 ± 119 (1.3x)* | 5986 ± 786 | 8975 ± 697 (1.5x) |

*Figures in bracket give fold improvement over and above the treatment in the column on immediate left.

The above examples give sufficient experimental evidence to illustrate that both the inventions i.e., heat pretreatment of particles and use of isopropanol can be incorporated in the standard protocols to obtain highly improved results. Both the modifications together gave 43 and 46 fold higher GUS activities (Table 5, Nonheated ethanol vs. heated isopropanol) for the old and the new particles respectively. Similarly, histochemical visualization of the number of blue spots showed 63 and 50 fold (Table 6) higher spread for the old and the new particles respectively. Increase in number of spots commensurate with the increase in GUS activity substantiates that the improved protocol invented by us enhances delivery of particles in an expression proficient manner. The particles prepared by our protocol do not visibly stick to walls of polypropylene tubes of a variety of local brands tested by us. The shot to shot results were highly reproducible. The coefficient of variation (standard deviation/mean) was only 6.7% for the heat pretreated isopropanol coated new particles as against 43% for the new particles prepared by conventional method. The results are in accordance with the claim that our method gives exceedingly superior delivery of biological material (DNA in the preferred example) and an extraordinarily high reproducibility of results. It allows the use of several years old particles stored without any special care. It also allows the applications of biolistic techniques without necessarily taking internal control to normalize results from independent shots.

EXAMPLE 6

This example illustrates that the invention described by us does not work only for the test plant tobacco but also for other important crop plants like rice (monocots). Here, gold particles were preheated, processed and coated with the DNA using isopropanol as per the invention, as described earlier. The particles were then bombarded on expanded leaves of rice plant. After bombardment the leaves were incubated on MS-agar medium, as described earlier. Expression of the GUS reporter gene was examined quantitatively by the fluorometeric method.

As seen from the Table 7, the improved method invented by us works equally well for the delivery of DNA to plants other then tobacco. Hence, the improved method works efficiently in principle, irrespective of the target tissue.

TABLE 7

Quantitative expression of glucuronidase in rice leaves by fluorimetric method using gold particles treated with both heat and isopropanol.

|  | GUS activity (pmol MU/h/mg protein) |
| --- | --- |
| Standard Method | 18 ± 8 |
| Invention - heat/isopropanol | 769 ± 132 |

EXAMPLE 7

This example illustrates that the preheating temperature of gold particles is not critical. Either unheated or particles preheated overnight at 90 to 150° C. temperature were coated with DNA using isopropanol, as described in the earlier examples. The effect of different temperatures during pretreatment was assessed by estimating gluconoridase (GUS) activity by the quantitative fluorimetric method, following bombardment on tobacco leaves, as described in the earlier examples.

TABLE 8

Effect of different temperatures of pre-treatment of gold particles as measured by quantitative expression of glucoronidase by fluorimetric method.

| Temperature | GUS activity (pmol/MU/h/mg protein) |
| --- | --- |
| Unheated | 17.5 ± 11 |
| 90° C. | 310 ± 76 (17x) |
| 110° C. | 484 ± 84 (27x) |
| 150° C. | 633 ± 106 (36x) |

As seen from Table 8, preheating the particles from 90° C.–150° C. gives beneficial effect. The extent of increase in GUS activity varied from 17-fold (90° C.) to 36-fold (150°

C.) in the above experiment. Thus preheating of gold particles at high temperatures leads to improvement of the DNA delivery. Though best improvement was obtained at 150° C. (36-fold) in the above example, it is preheating and not temperature per se that is important.

ADVANTAGES OF THE IMPROVED METHOD

As seen in the above examples, preheating the particles in dry oven and treatment with isopropanol instead of ethanol, enhances expression of the gene delivered in plant cells by several fold. Table 9 gives a comparison of the conventional and the improved methods in achieving functionally proficient delivery of plasmid DNA, taking gusA gene as the example. The results represent mean±standard deviation of six independent bombardment events. The results show about 50 fold comparative advantage in gene delivery, monitored by both the fluorimetric method (pmol MU formed/h/mg protein) and the histochemical methods (number of blue spots/shot), if both dry heating as well as isopropanol treatment were employed instead of the conventional method. The coefficient of variation for the improved method was only 6.7% compared to 43% for the particles prepared by the conventional method.

TABLE 9

Comparison of DNA delivery (measured as gusA expression) by the conventional and the improved protocols.

|   | Treatment | GUS activity | |
|---|---|---|---|
|   |   | Fluorimetric method (pmol MU/h/mg) | Histochemical method (No. of blue spots/shot) |
| A | Conventional method by Sanford et al, 1993 (No heating; use of ethanol) | 30 ± 13 | 178 ± 102 |
| B | Improvements | | |
|   | i) Heating alone | 689 ± 97 (23X)* | 5986 ± 786 (34X) |
|   | ii) Isopropanol alone | 326 ± 28 (11X) | 2618 ± 262 (15X) |
|   | iii) Heating as well as isopropanol treatment | 1395 ± 93 (47X) | 8976 ± 697 (50X) |

*Values in brackets give fold X improved over the conventional method.

What is claimed is:

1. An improved process for transporting a biological material into a living cell, a cell or tissue of a plant or a cell or tissue of an animal which comprises bombarding the living cell or tissue with a biological material coated on metal bead particles, wherein the metal bead particles are pretreated by heating the particles at a temperature ranging between 90–300° C. for a period ranging between 1 to 18 hours and thereafter coating the pretreated bead particles with a biological material using an organic solvent.

2. An improved process as claimed in claim 1 wherein the heating of the particles is carried out in a dry oven to allow removal of volatile materials.

3. An improved process as claimed in claim 1 wherein the particles used are beads selected from any biologically non reactive material from the group consisting of gold, palladium platinum or any alloy thereof.

4. An improved process as claimed in claim 1 wherein the heat treated particles are coated with the biological material using isopropanol as the organic solvent.

5. An improved process as claimed in claim 1 wherein the beads are selected from any biologically non reactive material from the group consisting of gold, palladium, platinum or any alloy thereof wherein the beads have been stored for a period of more than six months.

6. An improved process as claimed in claim 1 wherein the beads used have a diameter of from about 0.1 microns to about 3.0 microns.

7. An improved process as claimed in claim 1 wherein the biological material is DNA, RNA or other biologically active molecules.

8. An improved process as claimed in claim 1 wherein the biological material, which is DNA, RNA or other biologically active molecules, is delivered in cells or tissue using microprojectiles as carriers.

9. A process for studying transient or long term effects of biological molecules comprising bombarding living cells with a biologically active molecule coated on metal bead particles and observing the living cells, wherein the metal bead particles are pretreated by heating the particles at a temperature ranging between 90–300° C. for a period ranging between 1 to 18 hours and thereafter coating the pretreated bead particles with a biological material using an organic solvent.

10. A process as claimed in claim 9 wherein the biological material is DNA, RNA or other biologically active molecules.

* * * * *